United States Patent [19]
Reese, Sr.

[11] Patent Number: 5,279,545
[45] Date of Patent: Jan. 18, 1994

[54] HAND AND HAND AND WRIST BRACE

[76] Inventor: James L. Reese, Sr., 1120 NW. 203rd St., Miami, Fla. 33169

[21] Appl. No.: 24,257

[22] Filed: Mar. 1, 1993

[51] Int. Cl.$^5$ ............................................. A61F 5/04
[52] U.S. Cl. ........................................................ 602/21
[58] Field of Search .................. 602/20, 21, 22, 61, 602/63, 64; 273/166 R, 189 R, 189 A; 2/16

[56] References Cited

U.S. PATENT DOCUMENTS 4,088,318  5/1978  Massman ..................... 273/189 A
4,765,319  8/1988  Finnieston et al. ................ 602/21

Primary Examiner—Richard J. Apley
Assistant Examiner—Beverly A. Meindl
Attorney, Agent, or Firm—Malloy & Malloy

[57] ABSTRACT

A wrist brace to be worn on a user's forearm and hand so as to limit the range of motion of the user's wrist, the brace including a forearm member and a hand member, the forearm member including an elongate, rigid, yet resilient rear sheath adapted to be tightened about the forearm of a user, and the hand member including a rigid, yet resilient front sheath adapted to be tightened about the hand of a user, the front sheath and rear sheath being hingedly secured to one another so as to enable movement of the hand member relative to the forearm member, and accordingly, movement of the wrist of the user, to be regulated by at least one strap extending from the forearm member and at least one retaining loop protruding from the hand member, the strap on the forearm member being structured and disposed to pass through the loop on the hand member and be adjustably tightened utilizing a hook and loop fastener on an exposed surface of the strap.

6 Claims, 2 Drawing Sheets

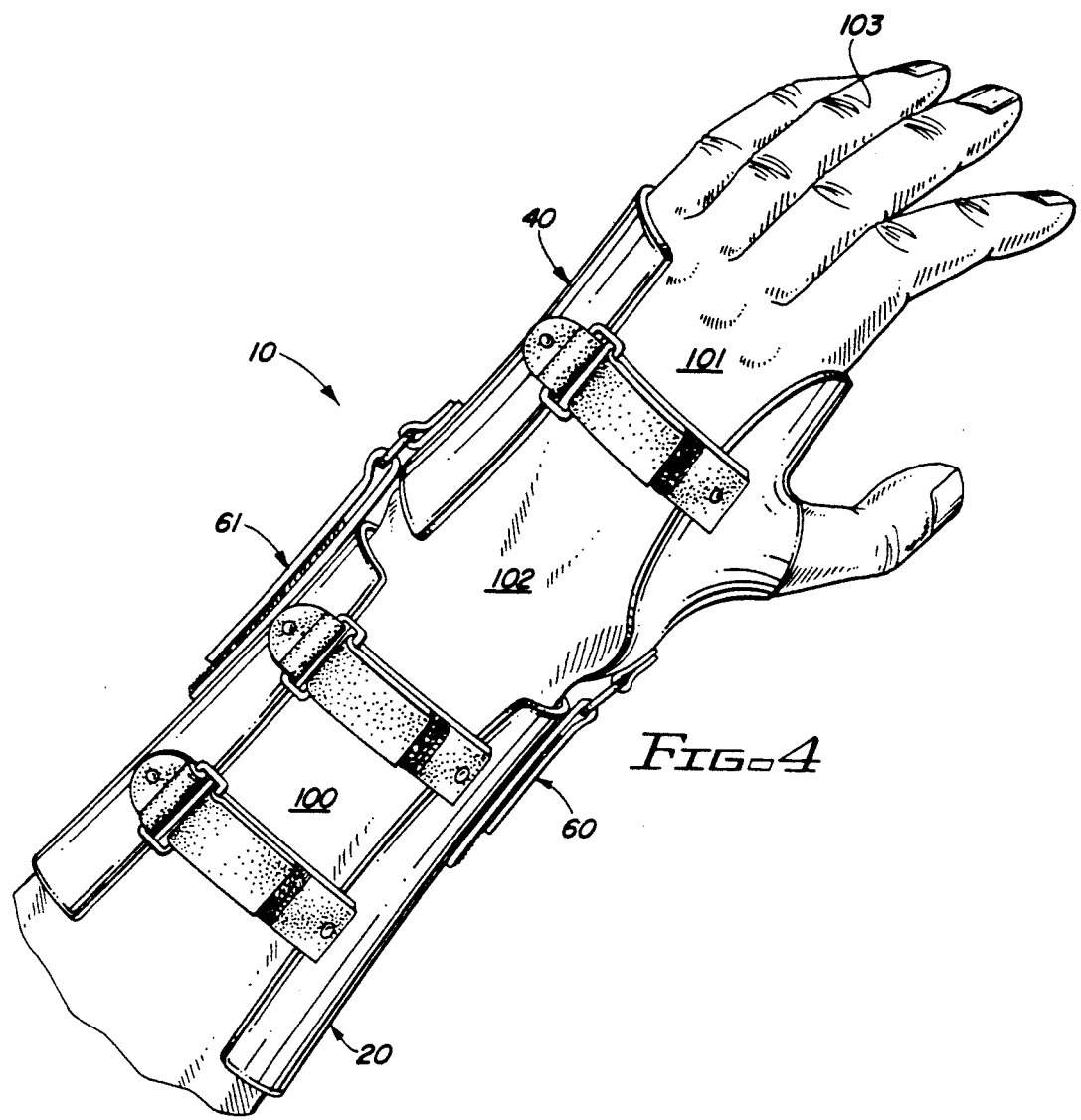
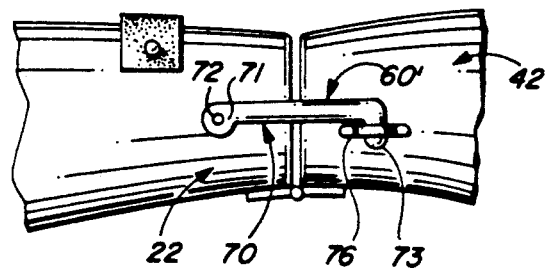

HAND AND HAND AND WRIST BRACE

BACKGROUND OF THE INVENTION

1. Field of the Invention

The present invention relates to a wrist brace adapted to limit the movement of the wrist of a user and be easily worn and adjusted, thereby enabling a user with limited manual dexterity to quickly and easily adjust the positioning of the wrist brace to a maximum comfort and/or optimal treatment orientation, the wrist brace being particularly effective for treatment of carpal tunnel syndrome or rehabilitation of a broken wrist or strained carpal ligament.

2. Description of the Related Art

Many wrist ailments, ranging from arthritis or a sprained wrist to a broken wrist or carpal tunnel syndrome require for their treatment that the range of movement of a person's wrist be limited and that adequate support be provided for the wrist such that wrist muscles do not get overstrained. Unfortunately, treatment of many of these ailments may require long periods of time during which a sufferer's wrist muscle may weaken or during which an individual must use their hands despite the wrist ailment. Such needs are evidenced by the sufferer of carpal tunnel syndrome, the treatment of which takes extended periods of time, or in a more specific instance, an athlete with a broken or sprained wrist who can continue to perform physically if the wrist is properly protected, securely disposed in a rehabilitating position, and does not hinder the use of their hand. A further important necessity involved with the use of a wrist brace regards the facilitated manipulation of the wrist brace by its user. Since individuals, when putting on the wrist brace by themselves are left with only one hand to work with, and often due to the nature of the ailment their other hand may lack strength or otherwise have limited manual dexterity, the wrist brace must be easy to put on and more importantly easy to adjust so as to position the wrist in its optimal position.

Existing in the art are many splint/brace assemblies which are significantly bulky, limit the use of an individual's hands, and are difficult to adjust by the user. For example, the reference to Corbett, U.S. Pat. No. 2,312,523, discloses an adjustable tension splint which includes a front hand grip which limits the use of a user's hand and requires the loosening and tightening of a plurality of screws in order to adjust the tension of the splint. Similarly, the derotation wrist brace of Carter, U.S. Pat. No. 5,002,044 utilizes a number of pins to limit the range of motion of parallel hinges on the brace. It would be substantially difficult for a user to adjust the brace to a more desirable position during use, and use of the hands would be limited. An adjustable wrist splint, such as that disclosed in Lindemann, U.S. Pat. No. 4,677,971, which enables lateral movement of the wrist is limited with regard to the disposition of the hand relative to the forearm and could not be utilized in a large variety of circumstances, much like the universal articulated splint of Deprospero, U.S. Pat. No. 4,719,906 which includes an elaborate hand splint wherein each finger on the hand is immobilized such that an individual cannot use their hand if necessary. The splint/braces of the prior art are not adapted to enable facilitated use and adjustment by the particular user and are generally directed at fixing the disposition of the wrist relative to the forearm without allowing a user to make quick and easy adjustments of the positioning as needed for their comfort and beneficial treatment. The brace of the present invention is adapted specifically to have multiple varying uses, be easy to put on by a user who will necessarily only have one hand to work with, and be quickly and easily adjustable by the individual user so as to assure that maximum comfort and benefit is achieved.

SUMMARY OF THE INVENTION

The present invention is directed towards a wrist brace to be worn on an individual so as to provide support and limit the movement of the individual's wrist. The wrist brace includes primarily a forearm member and a hand member. The forearm member includes primarily an elongate, rigid, yet resilient rear sheath. This rear sheath has a surrounding wall structure, an open distal end, an open proximal end, and an axial adjustment opening wherethrough an individual may insert their forearm. This rear sheath further includes adjustable rear tightening means spanning the axial adjustment opening. These tightening means are structured and disposed to secure the rear sheath about the user's forearm. The hand member of the wrist brace includes primarily a rigid, yet resilient front sheath. This front sheath includes a surrounding wall, an open proximal end, an open distal end, a thumb opening wherein an individual may insert their thumb, and an axial adjustment opening wherethrough an individual's hand is inserted into the hand member. Similarly to the rear sheath, the front sheath includes an adjustable front tightening means spanning the axial adjustment opening, the front tightening means securing the front sheath on the user's hand. The front sheath and the rear sheath are hingedly secured to one another along a lower surface, opposite the axial adjustment openings, of the proximal end of the front sheath and the distal end of the rear sheath. This hinge, along with movement regulating means, are adapted to limit and control the range of movement of the hand member relative to the forearm member, and accordingly the wrist of an individual user. These movement regulating means, which are adapted to be easy to adjust by the user, include at least one strap extending from the forearm member and at least one retaining loop protruding from the hand member. The strap on the forearm member is adapted to pass through the retaining loop on the hand member, and through the use of a hook and loop fastener on an exposed surface of the strap, to securely position the hand member in a select, adjusted position.

It is an object of the present invention to provide a wrist brace which is easy to put on by an individual utilizing only their single free hand.

Yet another object of the present invention is to provide a wrist brace which effectively limits the range of motion of an individual's wrist and supports the wrist so as to provide alleviation and treatment of a plurality of wrist ailments.

Still another object of the present invention is to provide a wrist brace which can be quickly and easily adjusted by the user utilizing only their free hand and which enables the hand which is within the brace to be useable.

BRIEF DESCRIPTION OF THE DRAWINGS

For a fuller understanding of the nature of the present invention, reference should be had to the following detailed description taken in connection with the accompanying drawings in which:

FIG. 4 is a top view of the wrist brace in use on an individual.

FIG. 5 is an isolated side view of a second embodiment of the movement regulating means of the present invention.

Like reference numerals refer to like parts throughout the several views of the drawings.

DETAILED DESCRIPTION OF THE PREFERRED EMBODIMENT

Figure 1:
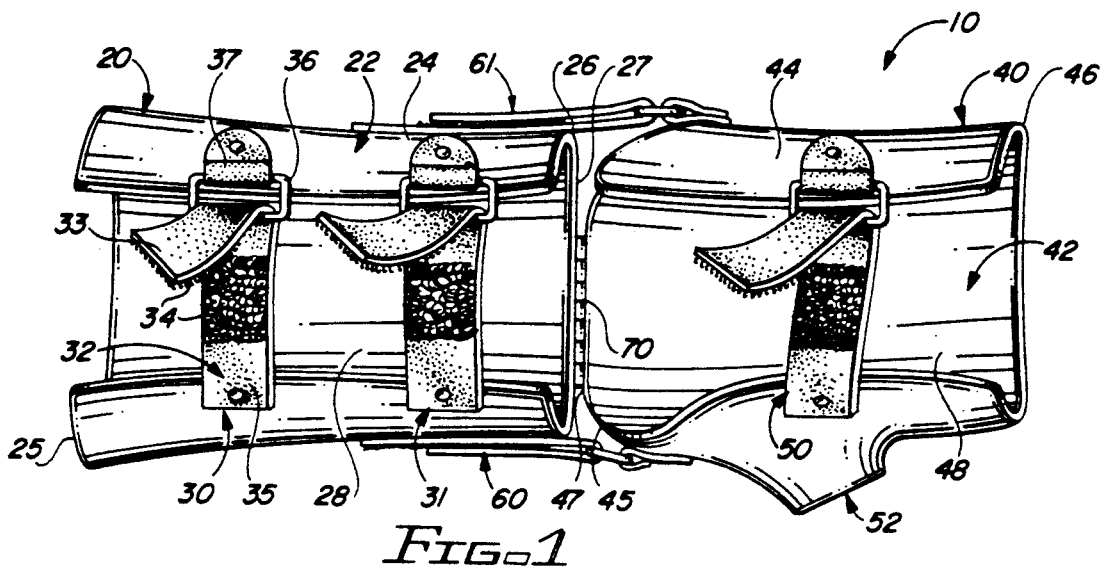
FIG. 1 is a top view of the wrist brace.
Figure 2:
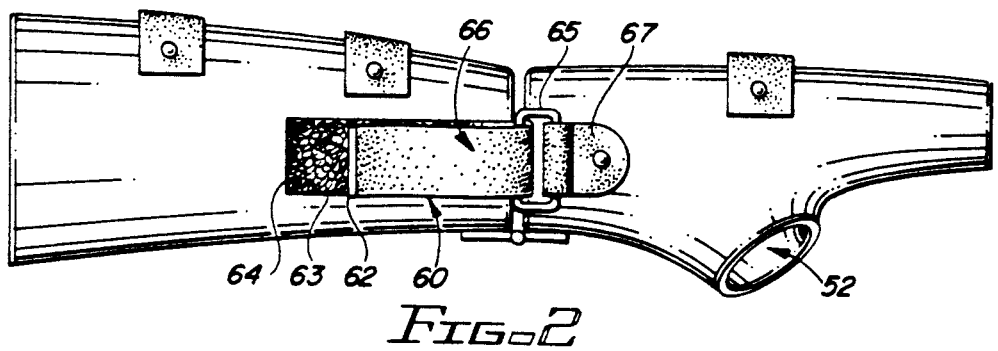
FIG. 2 is a right side view of the wrist brace.
Figure 3:
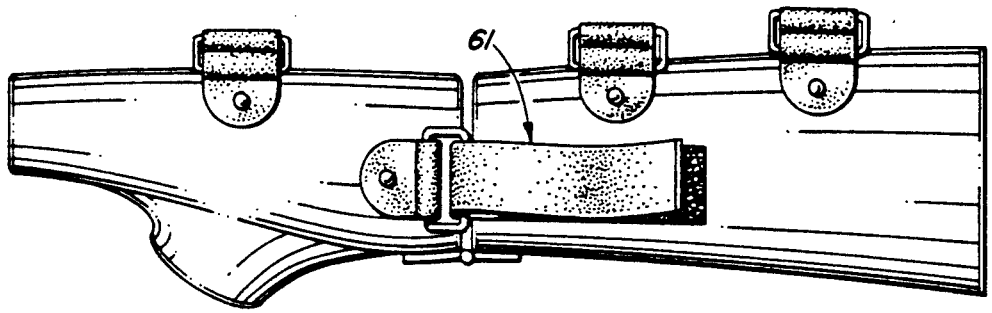
FIG. 3 is a left side view of the wrist brace.

Shown throughout FIGS. 1-5, the present invention is directed towards a wrist brace, generally indicated as 10. The wrist brace 10 includes primarily a forearm member 20 and a hand member 40. The forearm member 20 includes an elongate, rigid, yet resilient rear sheath 22 preferably formed of a rigid plastic which is lightweight and provides sufficient support and is movement constraining. The rear sheath 22 has a surrounding wall structure 24, which is generally C-shaped. This rear sheath 22 is adapted to receive a user's forearm 100 therein, and accordingly includes an open proximal end 25 and an open distal end 26 through which the user's forearm 100 protrudes from the rear sheath 22. Extending along a length of the rear sheath 22 is an axial adjustment opening 28. This axial adjustment opening 28 is formed in the surrounding wall structure 24 of the rear sheath 22, thereby giving it its general C-shape, and is adapted to enable the surrounding wall 24 of the rear sheath 22 to vary in dimensions as a result of the narrowing of the width of the axial adjustment opening 28, thereby conforming to forearms of varying sizes. This size is adjustable and secured at a desired dimension by adjustable rear tightening means 30 and 31 which span the axial opening 28 in the rear sheath 22 and provide for a secure, snug fit about the user's forearm 100. In the preferred embodiment, there are two adjustable rear tightening means 30 and 31, but this number may vary in accordance with the needs of a particular user.

The hand member 40, which is adapted to receive a user's hand 101 securely and supportably therein includes a rigid, yet resilient front sheath, also preferably formed of a rigid, lightweight plastic material. This front sheath 42 includes a surrounding wall 44, which also has a general C shape, an open proximal end 45, and an open distal end 46. Additionally, the front sheath 42 includes a thumb opening 52. The thumb opening 52 is preferably contoured into the front sheath 42 so as to provide a more comfortable and non-stressful fit. Further, the front sheath 42 may either be adapted to be worn on a right hand or left hand, and accordingly, the positioning of the thumb opening 52 will necessarily decide which hand it is to be used for. The user's hand 101 is held within the surrounding wall 44 of the front sheath 42 such that the wrist 102 protrudes from the open proximal end 45 and the fingers 103 extend from the open distal end 46. Similarly to the rear sheath 22, the front sheath 42 includes an axial adjustment opening 48 which defines the general C-shape of the surrounding wall 44 and enables appropriate tightening of the front sheath 42 about the user's hand 100. Spanning the axial adjustment opening 48 on the front sheath 42 are front tightening means 50. These front tightening means 50 are adapted to secure the front sheath 42 on the user's hand 100 and in the preferred embodiment includes only one front tightening means 50.

In the preferred embodiment, the adjustable rear tightening means 30 and 31 and the adjustable front tightening means 50 all include an elongate strap 32 secured to the surrounding wall 24 or 44 and adapted to extend across the axial adjustment opening 28 or 48. Disposed across the axial adjustment opening 28 or 48 from the strap 32 is a loop 36. The loop 36 is secured to the surrounding wall 24 or 44 by a material loop 37 and is disposed such that a free distal end 33 of the elongate strap 32 may pass through the loop 36. By pulling on the free distal end 33 of the strap 32, the width of the axial adjustment opening 28 or 48 is varied so as to assure a secure fit. Disposed on an exterior surface 35 of the strap 32 are hook and loop fastener pads 34. The hook and loop fastener pads 34 are disposed such that subsequent to passing through the retaining loop 36, the distal end 33 of the strap 32 may be secured in a desired, tightening location.

In order to regulate movement of a user's hand 101 relative to their forearm 100, and accordingly limit the movement of their wrist 102, the forearm member 20 is hingedly attached to the hand member 40 by an elongate hinge 70. The hinge 70 connects a lower surface 27 of the open distal end 26 of the rear sheath 22 with a lower surface 47 of the open proximal end 45 of the front sheath 42. Extending from the rear sheath 22 to the front sheath 42 are movement regulating means 60 and 61. The movement regulating means 60 and 61 are disposed on opposite sides from one another and are adapted to limit and control the movement of the hand member 40 relative to the forearm member 20. The movement regulating means 60 and 61 include primarily an elongate strap 66 secured to the surrounding wall 24 of the rear sheath 22. The strap 66 includes a free distal end 62 which is adapted to pass through a retaining loop 65 secured to the front sheath 42. This retaining loop 65 is secured to the front sheath 42 by means of a material loop 67, and by pulling on the free distal end 62 of the straps 66 on the movement regulating means 60 and 61, the hand member 40 may be securely disposed in a number of straight or bent locations relative to the forearm member 20, depending on the particular needs of a user. The strap 66 is secured in a desired position by means of hook and loop fastener pads 63 disposed on an exposed surface 64 of the strap 66. By utilizing two of the movement regulating means 60 and 61 and the strap 66 and retaining loop 65, the wrist brace is easily adjustable by an individual utilizing only their free hand and is substantially effective in assuring that the wrist brace 10 remains properly oriented throughout use.

Detailed in FIG. 5, an alternative embodiment of the movement regulating means 60' includes an elongate hook member 70. The hook member 70 is pivotally secured at its proximal end 71 to the surrounding wall 24 of the rear sheath 22 by means of a small rivet or screw 72 passing through the proximal end 71 of the hook member 70 into the rear sheath. Disposed on the front sheath 42 is a generally U-shaped retaining member 76. The retaining member 76 is structured and disposed to receive therein a hooked distal end 73 of the hook member 70 thereby regulating the movement of the sheaths 22 and 42.

Now that the invention has been described,

What is claimed is:

1. A hand and wrist brace comprising:

a forearm member and a hand member, said forearm member including an elongate, rigid, yet resilient rear sheath, said rear sheath including a surrounding wall structure, an open distal end, an open proximal end, and an axial adjustment opening, said rear sheath further including adjustable rear tightening means spanning said axial opening, said tightening means being structured and disposed to secure said rear sheath about a user's forearm, said hand member including a rigid, yet resilient front sheath, said front sheath including a surrounding wall, an open proximal end, an open distal end, a thumb opening, and an axial adjustment opening, said front sheath further including adjustable front tightening means spanning said axial adjustment opening in said front sheath and being structured and disposed to secure said front sheath on a user's hand, said front sheath and said rear sheath being hingedly secured to one another along a lower surface, opposite said axial adjustment opening, of said open proximal end of said front sheath and a lower surface, opposite axial adjustment opening, of said open distal end of said rear sheath, movement regulating means structured and disposed to limit and control movement of said hand member relative to said forearm member and, said movement regulating means including at least one strap extending from said forearm member and at least one retaining loop protruding from said hand member, said strap on said forearm member being structured and disposed to pass through said retaining loop on said hand member.

2. A hand and wrist brace as recited in claim 1 wherein said front sheath and said rear sheath are made of a substantially rigid, lightweight plastic material.

3. A hand and wrist brace as recited in claim 1 wherein said front sheath includes a contoured portion wherein said thumb opening is positioned so as to more closely conform said front sheath to the user's hand.

4. A hand and wrist brace as recited in claim 3 wherein said adjustable rear tightening means includes a pair of elongate straps secured to said surrounding wall structure in said rear sheath and spanning said axial adjustment opening in said rear sheath so as to be disposed opposite a corresponding pair of loops secured to said surrounding wall structure of said rear sheath, said straps being adapted to pass through said loops and be secured in a selected position by hook and loop fastener pads on an exposed surface thereof, thereby tightening said rear sheath properly about the user's forearm.

5. A hand and wrist brace as recited in claim 4 wherein said adjustable front tightening means includes an elongate strap secured to said surrounding wall structure of said front sheath and extending across said axial adjustment opening in said front sheath so as to engage an oppositely disposed loop secured to said surrounding wall structure of said front sheath, said strap being securable in a selected tightening position about said loop by hook and loop fastener pads disposed on an exposed surface of said strap of said front tightening means thereby securing said front sheath about the user's hand.

6. A hand and wrist brace as recited in claim 1 wherein said strap on said forearm member is substantially flexible and includes hook and loop fastener pads on an exposed surface thereof for adjustable tightening of said strap about said loop and accordingly adjustable positioning of said hand member relative to said forearm member.

* * * * *